United States Patent [19]

Mandai et al.

[11] Patent Number: 5,468,850
[45] Date of Patent: Nov. 21, 1995

[54] PROCESS FOR PREPARING HIGH 2-O-α-D-GLUCOPYRANOSYL-L-ASCORBIC ACID CONTENT PRODUCT

[75] Inventors: Takahiko Mandai; Masaru Yoneyama; Shuzo Sakai, all of Okayama, Japan

[73] Assignees: Kabushiki Kaisha Hayashibara; Seibutsu Kagaku Kenkyujo, both of Okayama, Japan

[21] Appl. No.: 964,303

[22] Filed: Oct. 21, 1992

[30] Foreign Application Priority Data

Oct. 23, 1991 [JP] Japan ................... 3-339282

[51] Int. Cl.⁶ .................. C07H 1/06; C07H 17/04; C07D 307/62
[52] U.S. Cl. ............. 536/18.5; 536/1.1; 536/124; 536/127; 536/4.1; 536/18.2; 536/18.6; 549/315
[58] Field of Search ................... 536/124, 18.6, 536/1.1, 127, 18.5; 549/315

[56] References Cited

U.S. PATENT DOCUMENTS

| 3,763,009 | 10/1973 | Suzuki et al. | 536/18.2 |
| 4,487,198 | 12/1984 | Miyake et al. | 435/198 |
| 5,137,723 | 8/1992 | Yamamoto et al. | 536/18.5 |

FOREIGN PATENT DOCUMENTS

| 425066 | 3/1990 | European Pat. Off. . |
| 398484 | 3/1990 | European Pat. Off. . |
| 48-38158 | 11/1973 | Japan . |
| 58-23799 | 2/1983 | Japan . |
| 135992 | 6/1991 | Japan . |
| 139288 | 6/1991 | Japan . |
| 3183492 | 8/1991 | Japan . |

OTHER PUBLICATIONS

Nippon Eiyo Shokuryo Gakkaishi, Journal of Japanese Society of Nutrition and Food Science, vol. 43, 1990.
Science and Industry, vol. 65, 1991, pp. 265–274.
Miyake and Suzuki, "Enzymatic Formation of New L–Ascorbic Acid Glycosides.", Vitamins, vol. 43, 1971 pp. 205–209.

Primary Examiner—Michael G. Wityshyn
Assistant Examiner—Everett White
Attorney, Agent, or Firm—Browdy and Neimark

[57] ABSTRACT

Disclosed is an industrial-scale preparation of a high 2-O-α-D-glucopyranosyl-L-ascorbic acid content product with an improved purity, the preparation comprising subjecting a solution containing 2-O-α-D-glucopyranosyl-L-ascorbic acid and a saccharide derivative of L-ascorbic acid exhibiting a direct reducing activity to an oxidation treatment, subjecting the resultant mixture ti column chromatography using a strongly-acidic cation exchange resin, and recovering the resultant high 2-O-α-D-glucopyranosyl-L-ascorbic acid content fraction. Thus, the preparatiobn has a great significance in the industrial field.

7 Claims, No Drawings

PROCESS FOR PREPARING HIGH 2-O-α-D-GLUCOPYRANOSYL-L-ASCORBIC ACID CONTENT PRODUCT

BACKGROUND OF THE INVENTION

1. Field of the Invention

The present invention relates to a process for preparing a high 2-O-α-D-glucopyranosyl-L-ascorbic acid content product, more particularly, to a process for preparing a high 2-O-α-D-glucopyranosyl-L-ascorbic acid content from a solution containing 2-O-α-D-glucopyranosyl-L-ascorbic acid and a saccharide derivative of L-ascorbic acid exhibiting a direct reducing activity.

2. Description of the Prior Art

As disclosed in Japanese Patent Laid-Open Nos. 135,992/91 and 139,288/91, 2-O-α-D-glucopyranosyl-L-ascorbic acid is a novel saccharide derivative of L-ascorbic acid which has the chemical structure shown by the formula I, a satisfiable stability and substantial no direct reducing activity, as well as being readily hydrolyzed in vivo to exert the inherent physiological activity of L-ascorbic acid. Formula I:

Formula I:

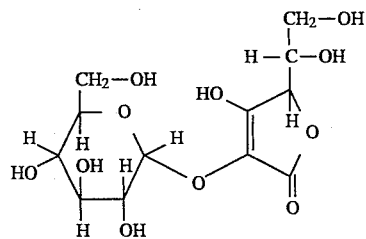

The industrial-scale preparations of 2-O-α-D-glucopyranosyl-L-ascorbic acid are, for example, a preparation as disclosed in Japanese Patent Laid-Open No. 183,492/91 comprising allowing a solution containing an α-glucosyl saccharide and L-ascorbic acid to the action of a saccharide-transferring enzyme together with or without glucoamylase to form a solution containing 2-O-α-D-glucopyranosyl-L-ascorbic acid and other concomitants; subjecting the resultant solution as a material solution to column chromatography using a strongly-acidic cation exchange resin; and recoverying the resultant high 2-O-α-D-glucopyranosyl-L-ascorbic acid content fraction; and, if necessary, further concentrating the fraction into a supersaturated solution to obtain a crystalline 2-O-α-D-glucopyranosyl-L-ascorbic acid.

During the study of a preparation of a high 2-O-α-D-glucopyranosyl-L-ascorbic acid content product, the present inventors found that a solution containing 2-O-α-D-glucopyranosyl-L-ascorbic acid and other concomitants as a material solution had a drawback in the step of column chromatography using a strongly-acidic cation exchange resin, i.e. there coexisted in such a material solution concomitants such as L-ascorbic acid and glucose which were separable with a relative easiness from 2-O-α-D-glucopyranosyl-L-ascorbic acid, and relatively-small amounts of unknown substances which substantially could not be separated from 2-O-α-D-gluco-pyranosyl-L-ascorbic acid and hindered the increment of the purity of a high 2-O-α-D-glucopyranosyl-L-ascorbic acid content fraction, as well as inhibiting the crystallization of 2-O-α-D-glucopyranosyl-L-ascorbic acid in its supersaturated solution.

The present inventors also found that the unknown substances, which were accumulated in a mother liquor in which a crystalline 2-O-α-D-glucopyranosyl-L-ascorbic acid had been removed, inhibited the crystallization of 2-O-α-D-gluco-pyranosyl-L-ascorbic acid in the mother liquor, and strongly lowered the yield of the crystal in the second- and third-crystallization steps.

It has been a great demand to reveal unknown substances coexisted in a solution of 2-O-α-D-glucopyranosyl-L-ascorbic acid prepared by a saccharide-transfer reaction, and to establish an industrial-scale preparation of a high-purity 2-O-α-D-glucopyranosyl-L-ascorbic acid in a relatively-high yield by removing concomitants with a relative easiness from a solution containing the concomitants and 2-O-α-D-gluco-pyranosyl-L-ascorbic acid.

SUMMARY OF THE INVENTION

The present inventors studied to establish a readily feasible industrial-scale preparation of a high-purity 2-O-α-D-glucopyranosyl-L-ascorbic acid high-content product by subjecting a solution containing 2-O-α-D-glucopyranosyl-L-ascorbic acid and other concomitants, which had been prepared by a saccharide-transfer reaction, to column chromatography using a strongly acidic-action exchange resin.

As a result, the present inventors found that in column chromatography using a strongly-acidic cation exchange resin 5-O-α-D-glucopyranosyl-L-ascorbic acid and 6-O-α-D-glucopyranosyl-L-ascorbic acid were unsatisfiable concomitants which rendered the separation of 2-O-α-D-glucopyranosyl-L-ascorbic acid difficult, hindered the increment of the purity of a high 2-O-α-D-glucopyranosyl-L-ascorbic acid content fraction, and inhibited the crystallization of 2-O-α-D-gluco-pyranosyl-L-ascorbic acid in its supersaturated solution.

It was found that 5-O-α-D-glucopyranosyl-L-ascorbic acid was a novel substance which had not been reported in any literature, and 6-O-α-D-glucopyranosyl-L-ascorbic acid was a known substance disclosed in Japanese Patent Publication No.38,158/73, and that both of which unlike 2-O-α-D-gluco-pyranosyl-L-ascorbic acid were saccharide derivatives of L-ascorbic acid exhibiting a direct reducing activity.

The present inventors studied on the properties of saccharide derivatives of L-ascorbic acid such as 2-O-α-D-glucopyranosyl-L-ascorbic acid exhibiting no direct reducing activity, and 5-O-α-D-glucopyranosyl-L-ascorbic acid and 6-O-α-D-glucopyranosyl-L-ascorbic acid exhibiting a direct reducing activity, and found that (i) 2-O-α-D-glucopyranosyl-L-ascorbic acid was readily separated from other saccharide derivatives of L-ascorbic acid exhibiting a direct reducing activity by a process comprising subjecting a solution containing 2-O-α-D-glucopyranosyl-L-ascorbic acid and the other saccharide derivatives to an oxidation treatment in order to selectively oxidize the other saccharide derivatives, and subjecting the resultant solution to column chromatography using a strongly-acidic cation exchange resin to fractionate 2-O-α-D-glucopyranosyl-L-ascorbic acid and the resultant oxides of the other saccharide derivatives; and that (ii) a high-purity 2-O-α-D-glucopyranosyl-L-ascorbic acid high-content product was preparable by the process in an industrial scale and in a relatively-high yield. Thus, the present inventors accomplished this invention.

The supersaturated solution of a high-purity 2-O-α-D-glucopyranosyl-L-ascorbic acid high-content product thus obtained was readily crystallized and the yield of which was relatively high, and these revealed that the present preparation was extremely advantageous as an industrial-scale preparation of a crystalline 2-O-α-D-glucopyranosyl-L-ascorbic acid.

DETAILED DESCRIPTION OF THE INVENTION

The present invention relates to a process for preparing a high 2-O-α-D-glucopyranosyl-L-ascorbic acid content product, more particularly, to a process for preparing a high 2-O-α-D-glucopyranosyl-L-ascorbic acid content product from a solution containing 2-O-α-D-glucopyranosyl-L-ascorbic acid and a saccharide derivative of L-ascorbic acid exhibiting a direct reducing activity.

The solutions containing 2-O-α-D-glucopyranosyl-L-ascorbic acid and a saccharide derivative of L-ascorbic acid exhibiting a direct reducing activity usable in the invention include those which contain 2-O-α-D-glucopyranosyl-L-ascorbic acid together with a saccharide derivative of L-ascorbic acid such as 5-O-α-D-glucopyranosyl-L-ascorbic acid and 6-O-α-D-glucopyranosyl-L-ascorbic acid. Examples of such solutions are a solution (I) which can be obtained by allowing a saccharide-transferring enzyme together with or without glucoamylase to act on a solution containing an α-glucosyl saccharide and L-ascorbic acid; a high 2-O-α-D-glucopyranosyl-L-ascorbic acid content solution (II) which can be obtained by subjecting the solution (I) to column chromatography using a strongly-acidic cation exchange resin; and a mother liquor which can be obtained by concentrating the solution (II) into a supersaturated solution, allowing to crystallize the super-saturated solution, separating the formed crystal, and recovering the resultant solution.

The wording "exhibiting a direct reducing activity" as referred to in the invention means, similarly as in L-ascorbic acid, an activity which reduces and decolors 2,6-dichlorophenolindophenol.

The L-ascorbic acid usable in the invention includes L-ascorbic acid in free acid form and L-ascorbates such as alkaline metal salts of L-ascorbic acid, alkaline-earth metal salts of L-ascorbic acid, and mixtures thereof.

Accordingly, L-ascorbic acid in free acid form, sodium ascorbates and calcium ascorbates of L-ascorbic acid can be suitably used in the invention as L-ascorbic acid in a saccharide-transfer reaction.

The wordings "α-glycosyl-L-ascorbic acid, 2-O-α-D-glucopyranosyl-L-ascorbic acid, 5-O-α-D-glucopyranosyl-L-ascorbic acid and 6-O-α-D-glucopyranosyl-L-ascorbic acid" as referred to in the invention mean those which are in free acid form and salts, as long as they can be used without any inconvenience.

In the case of subjecting a solution containing 2-O-α-D-glucopyranosyl-L-ascorbic acid and a saccharide derivative of L-ascorbic acid exhibiting a direct reducing activity to an oxidation treatment, one should choose a condition which predominantly oxidizes the saccharide derivative without acting on 2-O-α-D-glucopyranosyl-L-ascorbic acid as much as possible. For example, a method containing a step of subjecting such a solution to aerobic conditions such as agitation-aeration conditions can be advantageously used.

In this case, the oxidation treatment can be advantageously feasible under a slight acidic- or an alkaline pH-condition, or under the presence of an oxidation accelerator, for example, metal salts such as copper salts, ferric salts and ferrous salts; and activated charcoals such as a charcoal activated by steam or zinc chloride.

If necessary, an oxide such as hydrogen peroxide and potassium permanganate can be advantageously added to a solution to be oxidized.

It was revealed that the resultant solution containing 2-O-α-D-glucopyranosyl-L-ascorbic acid and an oxide of a saccharide derivative of L-ascorbic acid exhibiting a direct reducing activity (hereinafter abbreviated as "oxide of saccharide derivative of L-ascorbic acid") can be readily separated into 2-O-α-D-glucopyranosyl-L-ascorbic acid and an oxide of saccharide derivative of L-ascorbic acid by column chromatography using a strongly-acidic cation exchange resin.

The column chromatography using a strongly-acidic cation exchange resin employed in the invention will be described in detail hereinafter.

The strongly-acidic cation exchange resins advantageously usable in the invention include conventional styrene-divinylbenzene copolymers bonded with sulfonyl residues in $H^+$-form, alkaline metal form such as $Na^+$- and $K^+$-form, alkaline-earth metal form such as $Ca^{++}$- and $Mg^{++}$-form. Examples of commercialized products thereof are "DOWEX 50W-X8", a product of Dow Chemical Company, Midland, Mich., USA; "Amberlite CG-120", a product of Rohm & Hass Company, Philadelphia, Penna., USA; "XT-1022E" commercialized by Tokyo Chemical Industries, Tokyo, Japan; and "Diaion SK104", a product of Mitsubishi Industries Ltd., Tokyo, Japan.

The resins as mentioned above have an advantageous feature in fractionating a high 2-O-α-D-glucopyranosyl-L-ascorbic acid content fraction, as well as having a satisfiable thermostability and abrasion tolerance, and these render the resins advantageously useful in an industrial-scale preparation of a high 2-O-α-D-glucopyranosyl-L-ascorbic acid content product.

In the case of using as a material solution a solution containing the objective 2-O-α-D-glucopyranosyl-L-ascorbic acid together with concomitants such as D-glucose and an oxide of a saccharide derivative of L-ascorbic acid, the objective 2-O-α-D-glucopyranosyl-L-ascorbic acid can be readily recovered by feeding the material solution to a column packed with a strongly-acidic cation exchange resin, feeding the column with water to effect fractionation in order to obtain fractions in the order indicated, i.e. a fraction rich in an oxide of saccharide derivative of L-ascorbic acid, a fraction rich in an oxide of saccharide derivative of L-ascorbic acid and 2-O-α-D-glucopyranosyl-L-ascorbic acid, a fraction rich in 2-O-α-D-glucopyranosyl-L-ascorbic acid, a fraction rich in 2-O-α-D-glucopyranosyl-L-ascorbic acid and D-glucose, and a fraction rich in D-glucose; and recoverying the fraction rich in 2-O-α-D-glucopyranosyl-L-ascorbic acid.

In the case of fractionating a material solution by feeding it to a column, a previously-obtained fraction rich in 2-O-α-D-glucopyranosyl-L-ascorbic acid, for example, a fraction rich in an oxide of a saccharide derivative of L-ascorbic acid and 2-O-α-D-glucopyranosyl-L-ascorbic acid and a fraction rich in 2-O-α-D-glucopyranosyl-L-ascorbic acid and D-glucose can be fed to the column before or after the feeding of the material solution, or fed to the column along with the material solution. Thereby, the amount of water required in the fractionation step is reduced and a high 2-O-α-D-glucopyranosyl-L-ascorbic acid content product can be advantageously prepared at a relatively-high concentration and in a relatively-high yield.

The fractionation methods usable in the invention include fixed-bed-, moving-bed- and simulated-moving-bed-methods.

The present high 2-O-α-D-glucopyranosyl-L-ascorbic acid content product thus obtained, preferably a high 2-O-α-D-glucopyranosyl-L-ascorbic acid content product with a purity of 70 w/w % or higher, is much more stabler than intact L-ascorbic acid and readily handleable even if the product is in the form of solution or syrup prepared by concentrating the solution.

The present high 2-O-α-D-glucopyranosyl-L-ascorbic acid content product and a preparation of a crystalline 2-O-α-D-glucopyranosyl-L-ascorbic acid will be described hereinafter.

The high 2-O-α-D-glucopyranosyl-L-ascorbic acid content product for the crystallization of 2-O-α-D-glucopyranosyl-L-ascorbic acid usable in the invention substantially does not have a saccharide derivative of L-ascorbic acid exhibiting a direct reducing activity which inhibits the crystallization of 2-O-α-D-glucopyranosyl-L-ascorbic acid. Because of this, the crystallization is extremely facilitated and the yield is relatively-high. The crystallization methods usable in the invention include a method comprising placing a supersaturated solution of 2-O-α-D-glucopyranosyl-L-ascorbic acid with a relatively-high temperature, i.e. a temperature of 20°–60° C., coexisting a seed crystal, preferably at a concentration of 0.1–10 w/w %, and gradually cooling the resultant mixture under a gentle-stirring condition to accelerate the crystallization and to form a massecuite.

The present crystalline 2-O-α-D-glucopyranosyl-L-ascorbic acid is readily crystallized by adding a supersaturated solution of 2-O-α-D-glucopyranosyl-L-ascorbic acid with a crystalline 2-O-α-D-glucopyranosyl-L-ascorbic acid as a seed crystal.

The methods to prepare a crystalline 2-O-α-D-glucopyranosyl-L-ascorbic acid from a massecuite usable in the invention are, for example, conventional separation, block-pulverization, fluidized-bed granulation and spray-drying as long as the crystalline 2-O-α-D-glucopyranosyl-L-ascorbic acid is obtained.

Although the properties of the crystalline 2-O-α-D-glucopyranosyl-L-ascorbic acid thus obtained are varied dependently on the purity and crystallinity, the crystalline 2-O-α-D-glucopyranosyl-L-ascorbic acid has a satisfiable free-flowing ability, as well as being substantially non-hygroscopic or free of hygroscopicity and free of solidification. The advantageous properties of the crystalline 2-O-α-D-glucopyranosyl-L-ascorbic acid are as follows:

(1) Exhibiting no direct reducing activity and being extremely stable. The crystal, unlike L-ascorbic acid, hardly exhibits maillard reaction. Because of these, it does not cause an unnecessarily reaction even in the presence of amino acids, peptides, proteins, lipids, saccharides and biologically active substances, and stabilizes these substances.

(2) When it is hydrolyzed, it forms L-ascorbic acid which exhibits a reducing activity and anti-oxidation activity similarly as in L-ascorbic acid.

(3) It is readily hydrolyzed by in vivo enzyme into L-ascorbic acid and D-glucose to exert the inherent activity of L-ascorbic acid. The physiological activity of the crystal can be augmented when used in combination with vitamins E and/or P.

(4) It is synthesized in vivo when orally taken along with an α-glucosyl saccharide and L-ascorbic acid, and metabolized in vivo. Because of this, it is extremely safe.

(5) Although it is substantially non-hygroscopic or free of hygroscopicity, it has a relatively-high solubility in water, and can be advantageously used as a vitamin C-enriched agent, taste-improving agent, acid- imparting agent and stabilizer in vitamins in the form of powder, granule and tablet and in food products such as cream filling, chocolate, chewing gum, powdered juice and premix seasoning.

(6) It has a substantial non-hygroscopicity or free hygroscopicity, as well as having a satisfiable handleability and free-flowing ability because of its free solidification. Because of these, it can more reduce the labour costs in the packaging, transportation and storage than a non-crystal line 2-O-α-D-glucopyranosyl-L-ascorbic acid.

The following experiments will explain the present invention in detail.

EXPERIMENT 1

Formation and separation of unknown substance

Thirty parts by weight of dextrin (dextrose equivalent (DE) about 6) was dissolved in 40 parts by weight of water by heating, and the solution was added with 7 parts by weight of L-ascorbic acid under reducing conditions, further added with 250 units/g dextrin of cyclomaltodextrin glucano-transferase, based on the weight of the dry solid (d.s.b.), commercialized by Hayashibara Biochemical Laboratories, Inc., Okayama, Japan, and allowed to react at pH 5.6 and 60° C. for 40 hours.

High-performance liquid chromatography (HPLC) analysis of the reaction mixture revealed that about 65% of L-ascorbic acid was converted into α-glycosyl-L-ascorbic acid, said HPLC system and its conditions comprising "LC-6A" column, a pump of Shimadzu Seisakusho Ltd., Kyoto, Japan; "Wakopak WB T-330", a column of Wako Pure Chemical Industries, Ltd., Osaka, Japan; "RI-7520", a differential refractometer of Eluma Optical Works Ltd., Tokyo, Japan; "875-UV", a uv-detector of Japan Spectroscopic Co., Ltd., Tokyo; 0.01 w/v % nitric acid as an eluate; and a flow rate of 0.5 ml/minute.

The reaction mixture was filtered with a UF-membrane filter to recover the remaining enzyme, and the resultant filtrate was adjusted to 50° C. and pH 5.0, added with 100 units/g dextrin of glucoamylase, d.s.b., and allowed to react for 6 hours.

The resultant mixture was heated to inactivate the remaining enzyme, decolored and filtered with an activated charcoal, and, in accordance with the method of column chromatography disclosed in Japanese Patent Laid-Open No.23, 799/83, the resultant filtrate was concentrated and subjected to column chromatography using a column packed with "DOWEX 50W-X4 ($Ca^{++}$-form)", a strongly-acidic cation exchange resin commercialized by Dow Chemical Co., Midland, Mich., USA. Thus, a high 2-O-α-D-glucopyranosyl-L-ascorbic acid content fraction was recovered, subjected to a column packed with a cation exchange resin ($H^+$-form) to effect demineralization and purification, and concentrated in vacuo to give a concentration of about 77 w/w %. The concentrate was placed in a crystallizer, added with a 2-O-α-D-glucopyranosyl-L-ascorbic acid seed crystal, adjusted to 40° C., gradually cooled to 20° C. over a period of 2 days under a gentle-stirring condition, and fed to a basket-type centrifuge to remove or separate a crystalline 2-O-α-D-glucopyranosyl-L-ascorbic acid. Thus, a first mother liquor was obtained in the yield of about 50% against the material L-ascorbic acid, d.s.b.

The first mother liquor was concentrated in vacuo similarly as above to effect recrystallization of 2-O-α-D-glucopyranosyl-L-ascorbic acid, and the resultant crystal was separated or removed to obtain a second mother liquor in the yield of about 25% against the material L-ascorbic acid, d.s.b.

HPLC analysis of the second mother liquor revealed that 2-O-α-D-glucopyranosyl-L-ascorbic acid and L-ascorbic acid were respectively detected at the positions of 18.7 and 29.7 minutes, while peaks of unknown substances at the positions of 21.7 and 23.1 minutes, which were located between the above two positions, were detected and named as substances "X" and "Y" provisionally.

The contents of the substances X and Y in the second mother liquor were respectively about 10 w/w %, d.s.b., and each substance had about 65 w/w %, d.s.b., of 2-O-α-D-glucopyranosyl-L-ascorbic acid.

In order to isolate the substances X and Y from the second mother liquor, a relatively-large amount of coexisting 2-O-α-D-glucopyranosyl-L-ascorbic acid should have been removed.

The present inventors studied the conditions to remove 2-O-α-D-glucopyranosyl-L-ascorbic acid, and found that 2-O-α-D-glucopyranosyl-L-ascorbic acid was more readily hydrolyzed than the substances X and Y under a relatively-high acidic- and temperature-condition. Thus, we removed 2-O-α-D-glucopyranosyl-L-ascorbic acid by using this hydrolysis method.

The method was as follows: The second mother liquor was adjusted to give a concentration of 25 w/w %, adjusted to pH 1.7 by the addition of hydrochloric acid, and allowed to predominantly hydrolyze 2-O-α-D-glucopyranosyl-L-ascorbic acid. Thereafter, the resultant solution was cooled and fed to a column packed with an anion exchange resin (OH$^-$-form) to adsorb the substances X and Y thereon, and the column was washed with water and fed with 0.5N hydrochloric acid to obtain a solution containing the substances X and Y.

The resultant solution was subjected to an HPLC system wherein 0.01M $NaH_2PO_4$-$H_3PO_4$ (pH 2.0) was used as an eluate and a flow rate was 4.5 ml/minute; said HPLC system comprising "Model 510", a pump of Japan Waters Co., Tokyo, Japan; "D-ODS-5", a column of YMC Co., Ltd., Kyoto, Japan; and a uv-detector. Thereafter, a fraction rich in substance X or Y was recovered, and further deionized with "Micro acilyzer G1" equipped with "Cartridge AC-110", a deionizer commercialized by Asahi Chemical Industry, Co., Ltd., Tokyo, Japan; concentrated and lyophilized to obtain a powder of X or Y in the yield of about 20% against the content of the substance X or Y in the material mother liquor, d.s.b.

HPLC analysis of the substances X and Y revealed that the purities of the substances X and Y were respectively about 98 w/w %, d.s.b., and about 97 w/w %, d.s.b.

EXPERIMENT 2

Physicochemical property

The physicochemical properties of the high-purity substances X and Y in Experiment 1 will be described hereinafter.

(a) Elemental analysis Calculated; C=42.6%, H=5.36% Found (substance X); C=42.4%, H=5.37% Found (substance Y); C=42.5%, H=5.37% (for chemical formula $C_{12}H_{18}O_{11}$)

(b) Ratio of glucose and L-ascorbic acid Calculated; Glucose: L-ascorbic acid=1:1 Found (substance X); Glucose: L-ascorbic acid=1.00 : 1.05 Found (substance Y); Glucose: L-ascorbic acid =1.00 : 0.99

Note : The content of glucose was determined by the anthrone-sulfuric acid method, and the content of L-ascorbic acid was determined by the indophenol-xylene method.

(c) Ultraviolet absorption spectrum The substances X and Y showed the maximum absorption spectra at 243 nm in a solution of pH 2.0, and at 265 nm in a solution of pH 7.0.

(d) Hydrolysis by enzyme of small intestinal membrane In accordance with the method reported by Okada et al. in *Journal of Japanese Society of Nutrition and Food Science*, Vol.43, No.1, pp.23–29 (1990), the substances X and Y were subjected to the hydrolysis test using an enzyme of a small intestinal membrane, and it was revealed that the substance X was readily hydrolyzed but the substance Y was not substantially hydrolyzed.

(e) NMR spectrum The nmr spectrum ($^{13}$C-NMR) of the substance X or Y showed 12 signals, and this meant all 12 carbons in each substance shifted differently. Each signal was assigned to α-D-glucopyranose and L-ascorbic acid as a standard substance, and the chemical shifts of the substances X and Y, as well as the standard substances, were as shown in Table 1.

TABLE 1

|  | L-Ascorbic acid | Substance X (A) | Substance Y (A) |
| --- | --- | --- | --- |
| C-1 | 174.0 | 176.8 | 176.7 |
| C-2 | 118.8 | 119.9 | 120.3 |
| C-3 | 156.4 | 161.4 | 160.4 |
| C-4 | 77.1 | 78.8 | 79.4 |
| C-5 | 69.9 | 77.2 | 70.8 |
| C-6 | 63.1 | 63.3 | 70.2 |
|  | α-D-Glucopyranose | Substance X (B) | Substance Y (B) |
| C-1 | 93.3 | 101.1 | 101.5 |
| C-2 | 72.8 | 75.1 | 74.9 |
| C-3 | 74.2 | 75.7 | 75.9 |
| C-4 | 70.9 | 71.8 | 72.5 |
| C-5 | 72.9 | 74.3 | 74.3 |
| C-6 | 62.3 | 62.9 | 63.5 |

Note: The symbol "A" means L-ascorbic acid residue and the symbol "B" means α-D-glucopyranose residue.

Based on the results in Table 1, it is determined that the substance X is a novel substance having the structure as shown in the formula 2, i.e. 5-O-α-D-glucopyranose-L-ascorbic acid; and the substance Y is a known substance having the structure as shown in formula 3, i.e. 6-O-α-D-glucopyranosyl-L-ascorbic acid.

Formula 2:

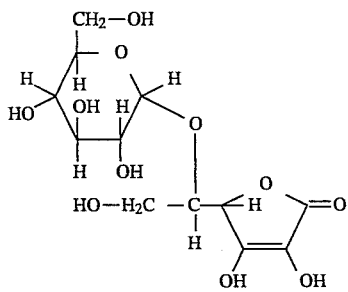

Formula 3:

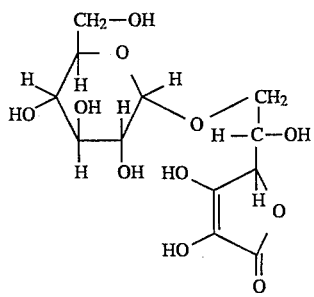

EXPERIMENT 3

Oxidation treatment

2-O-α-D-Glucopyranosyl-L-ascorbic acid, 5-O-α-D-glucopyranosyl-L-ascorbic acid, 6-O-α-D-glucopyranosyl-L-ascorbic acid, and a second mother liquor, all of which were prepared by the method in Experiment 1, were respectively adjusted to give a concentration of 10 w/w % and pH 5.0, and each solution thus obtained was added with 5 w/w %, d.s.b., of a charcoal activated by steam, and stirred at 27° C. for 24 hours under agitation-aeration conditions, followed by the oxidization of 5-O-α-D-glucopyranosyl-L-ascorbic acid, 6-O-α-D-glucopyranosyl-L-ascorbic acid and a saccharide derivative of L-ascorbic acid contained in the second mother liquor and the disappearance of their inherent uv-absorption spectra.

2-O-α-D-Glucopyranosyl-L-ascorbic acid, contained in its aqueous solution or in a second mother liquor, showed a satisfiable stability without exhibiting no quantitative- and qualitative-changes.

EXPERIMENT 4

Column chromatography using strongly-acidic cation exchange resin

Either intact second mother liquor prepared by the method in Experiment 1; or a solution which had been prepared by subjecting the second mother liquor to an oxidation treatment by the method in Experiment 3, removing the resultant activated charcoal, and demineralizing the resultant solution with a strongly-acidic cation exchange resin ($H^+$-form); was subjected as a material solution to column chromatography using a column packed with "XT-1016 ($H^+$-form)", a strongly-acidic cation exchange resin commercialized by Tokyo Chemical Industries, Tokyo, Japan, in accordance with the method disclosed in Japanese patent Laid-Open No.23,799/83.

In the case of using the intact second mother liquor, 2-O-α-D-glucopyranosyl-L-ascorbic acid and relatively-small amounts of 5-O-α-D-glucopyranosyl-L-ascorbic acid and 6-O-α-D-glucopyranosyl-L-ascorbic acid exhibiting a direct reducing activity exhibited the same chromatographic pattern, and this rendered the separation of them difficult.

It was found that the second mother liquor treated by the oxidation treatment was eluted and fractionated in the order indicated, i.e. a fraction rich in an oxide of saccharide derivative of L-ascorbic acid, a fraction rich in an oxide of saccharide derivative of L-ascorbic acid and 2-O-α-D-glucopyranosyl-L-ascorbic acid, and a fraction rich in 2-O-α-D-glucopyranosyl-L-ascorbic acid. Thus, the separation of 2-O-α-D-glucopyranosyl-L-ascorbic acid and the oxide was readily feasible in an industrial-scale.

The examples of the present invention will be described hereinafter.

EXAMPLE 1

Thirty parts by weight of dextrin (DE about 6) was dissolved in 40 parts by weight of water while heating, and the solution was added with 7 parts by weight of L-ascorbic acid under reducing conditions, added with 250 units/g dextrin of cyclodextrin glucanotransferase, d.s.b., and allowed to react at pH 5.6 and 60° C. for 40 hours.

The reaction mixture was filtered with a UF-membrane filter to collect and remove the remaining enzyme, and the filtrate was adjusted to 50° C. and pH 5.0, added with 100 units/g dextrin of glucoamylase, d.s.b., and allowed to react for 6 hours.

The resultant mixture was heated to inactivate the remaining enzyme and decolored and filtered with an activated charcoal. The filtrate was concentrated and subjected to column chromatography using "DOWEX 50W-X4 ($Ca^{++}$-form)", a strongly-acidic cation exchange resin commercialized by Dow Chemical Co., Midland, Michigan, USA, followed by recoverying a high 2-O-α-D-glucopyranosyl-L-ascorbic acid content fraction.

HPLC analysis of the fraction revealed that it contained 90 w/w % 2-O-α-D-glucopyranosyl-L-ascorbic acid, 2.5 w/w % 5-O-α-D-glucopyranosyl-L-ascorbic acid and 2.5 w/w % 6-O-α-D-glucopyranosyl-L-ascorbic acid, d.s.b.

The fraction was adjusted to give a concentration of about 36 w/w % and pH 4.0, and the resultant solution was added with 0.1 w/w %, d.s.b., of ferric sulfate, and subjected to an oxidation treatment at 30° C. for 20 hours under agitation-aeration conditions. Similarly as the above method, the resultant mixture was subjected to column chromatography using a strongly-acidic cation exchange resin to recover a high 2-O-α-D-glucopyranosyl-L-ascorbic acid content fraction.

The fraction thus obtained was purified by demineralizing it with a strongly-acidic cation exchange resin ($H^+$-form), and the resultant filtrate was concentrated in vacuo into a solution having a concentration of about 77 w/w % which was then placed in a crystallizer, added with a 2 w/w % 2-O-α-D-glucopyranosyl-1-ascorbic acid seed crystal, heated to 40° C., and gradually cooled to 20° C. under a gentle-stirring condition over a period of 2 days. The resultant mixture was fed to a basket-type centrifuge to obtain a crystalline 2-O-α-D-glucopyranosyl-L-ascorbic acid in the yield of about 50% against the material L-ascorbic acid, d.s.b.

The product exhibits no direct reducing activity but exhibits a satisfiable stability and physiological activity, and because of these it can be used in food products, cosmetics and agents of anti-susceptive diseases as a vitamin P-enriched agent, taste-imparting agent, acid-imparting agent, stabilizer, quality-improving agent, antioxidant, biological activator, uv-absorbent, pharmaceutical material and chemical product.

EXAMPLE 2

Nine parts by weight of dextrin (DE 10) was dissolved in 20 parts by weight of water while heating, and the mixture was added with 3 parts by weight of L-ascorbic acid under reducing conditions, and further added with 150 units/g dextrin of cyclodextrin glucanotransferase, d.s.b., and allowed to react at pH 5.5 and 65° C. for 40 hours.

HPLC analysis of the reaction mixture revealed that about 65 w/w % L-ascorbic acid was converted into α-glycosyl-L-ascorbic acid.

The reaction mixture was heated to inactivate the remaining enzyme, adjusted to 55° C. and pH 4.5, added with 50 units/g dextrin of glucoamylase, d.s.b., and allowed to react for 24 hours.

The resultant mixture was heated to inactivate the remaining enzyme and decolored and filtered with an activated charcoal. The filtrate was fed to a column packed with a cation exchange resin ($H^+$-form) to effect demineralization, and then fed to a column packed with an anion exchange resin ($OH^-$-form) to adsorb anions thereon. The column of anion exchange resin was washed with water to remove D-glucose and fed with 0.5N hydrochloric acid. The effluent was concentrated and subjected to column chromatography using a column packed with a strongly-acidic cation exchange resin ($H^+$-form) to obtain a high 2-O-α-D-glucopyranosyl-L-ascorbic acid content fraction.

The fraction was concentrated in vacuo into an about 76 w/w % solution which was then placed in a crystallizer, added with a 1 w/w % 2-O-α-D-glucopyranosyl-L-ascorbic acid seed crystal, heated to 40° C., and gradually cooled to 20° C. over a period of 2 days under a gentle-stirring condition. The resultant mixture was fed to a basket-type centrifuge to separate a crystalline 2-O-α-D-glucopyranosyl-L-ascorbic acid, followed by recoverying a mother liquor in the yield of about 55%, d.s.b.

HPLC analysis of the mother liquor revealed that it contained about 80 w/w % 2-O-α-D-glucopyranosyl-L-ascorbic acid, about 5 w/w % 5-O-α-D-glucopyranosyl-L-ascorbic acid, and about 5 w/w % 6-O-α-D-glucopyranosyl-L-ascorbic acid, d.s.b.

The mother liquor was adjusted to give a concentration of 18 w/w % and pH 5.0, added with 0.5 w/w %, d.s.b., of a charcoal activated by zinc chloride, and subjected to an oxidation treatment at 50° C. for 20 hours. Similarly as the above method, the resultant mixture was subjected to column chromatography using a strongly-acidic cation exchange resin to recover a high 2-O-α-D-glucopyranosyl-L-ascorbic acid content fraction which was then demineralized with an ion-exchange resin and concentrated in vacuo. In accordance with the method in Example 1, the concentrate was crystallized and subjected to separation, followed by recoverying a crystalline 2-O-α-D-glucopyranosyl-L-ascorbic acid in the yield of about 55% against the mother liquor, d.s.b.

Similarly as the product in Example 1, the product can be advantageously used in food products, cosmetics and agents of anti-susceptive diseases.

EXAMPLE 3

A mother liquor prepared by the method in Example 2 was adjusted to give a concentration of 20 w/w % and pH 7.5, and subjected to an oxidation treatment at 50° C. for 48 hours under agitation-aeration conditions. In accordance with the method in Example 2, the resultant mixture was subjected to column chromatography using a strongly-acidic cation exchange resin to recover a high 2-O-α-D-glucopyranosyl-L-ascorbic acid content fraction which was then demineralized with an ion-exchange resin and concentrated in vacuo. In accordance with the method in Example 1, the resultant concentrate was crystallized and subjected to separation, followed by recoverying a crystalline 2-O-α-D-glucopyranosyl-L-ascorbic acid in the yield of about 53% against the mother liquor, d.s.b.

Similarly as the product in Example 1, the product can be advantageously used in food products, cosmetics and agents of anti-susceptive diseases.

As described above, the present invention facilitates the separation of 2-O-α-D-glucopyranosyl-L-ascorbic acid and an oxide of saccharide derivative of L-ascorbic acid by subjecting a solution containing 2-O-α-D-glucopyranosyl-L-ascorbic acid and a saccharide derivative of L-ascorbic acid exhibiting a direct reducing activity to an oxidation treatment, and subjecting the resultant mixture to column chromatography using a strongly-acidic cation exchange resin. Thus, the present invention provides a high 2-O-α-D-glucopyranosyl-L-ascorbic acid content fraction with an improved purity, facilitates the crystallization of 2-O-α-D-glucopyranosyl-L-ascorbic acid and improves the yield.

Accordingly, the present invention has a great significance in the industrial field as a preparation of a high 2-O-α-D-glucopyranosyl-L-ascorbic acid content product.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for preparing a high 2O-α-D-glucopyranosyl-L-ascorbic acid content product from a solution containing 2-O-α-D-glucopyranosyl-L-ascorbic acid and a saccharide derivative of L-ascorbic acid exhibiting a direct reducing activity, said product being substantially free of direct reducing activity 5-O-α-D-glucopyranosyl-L-ascorbic acid and 6-O-α-D-glucopyranosyl-L-ascorbic acid, which process comprises:

(a) allowing a saccharide transferring enzyme optionally with glucoamylase to act on a solution containing an α-glucosyl saccharide and L-ascorbic acid to form 2-O-α-D-glucopyranosyl-L-ascorbic acid;

(b) subjecting the resultant solution containing 2-O-α-D-glucopyranosyl-L-ascorbic acid and a saccharide derivative of L-ascorbic acid exhibiting a direct reducing activity to an oxidation treatment under aerobic conditions and optionally in the presence of an oxidation-accelerating effective amount of an acid, alkali, metal salt oxidation accelerator, or activated charcoal to oxidize said saccharide derivative of L-ascorbic acid to substantial completeness and provide a solution containing 2-O-α-D-glucopyranosyl-L-ascorbic acid and an oxide of said saccharide derivative of L-ascorbic acid;

(c) fractionating the solution from step (b) by column chromatography using a strongly acidic-acidic cation exchange resin to elute, in sequence, (i) a fraction rich in said oxide of said saccharide derivative of L-ascorbic acid, (ii) a fraction rich in a mixture of said oxide of said saccharide derivative of L-ascorbic acid and 2-O-α-D-glucopyranosyl-L-ascorbic acid, and (iii) a fraction rich in said 2-O-α-D-glucopyranosyl-L-ascorbic acid; and (d) recovering the resultant high 2-O-α-D-glucopyranosyl-L-ascorbic acid content product substantially free of direct reducing activity 5-O-α-D-glucopyranosyl-L-ascorbic acid and 6-O-α-D-glucopyranosyl-L-ascorbic acid.

2. The process of claim 1, wherein said saccharide derivative of L-ascorbic acid is one or more saccharide derivatives of L-ascorbic acid exhibiting a direct reducing activity consisting of 5-O-α-D-glucopyranosyl-L-ascorbic acid and 6-O-α-D-glucopyranosyl-L-ascorbic acid.

3. The process of claim 1, wherein the step (b) is effected under a slight acidic- or an alkaline pH-condition.

4. The process of claim 1, wherein the step (b) is effected in the presence of said metal salt oxidation accelerator.

5. The process of claim 1, wherein said high 2-O-α-D-glucopyranosyl-L-ascorbic acid content product contains at least 70 w/w % 2-O-α-D-glucopyranosyl-L-ascorbic acid, on a dry solid basis.

6. The process of claim 1, wherein the step (c) further containsi a step of concentrating the resultant high 2-O-α-D-glucopyranosyl-L-ascorbic acid content fraction into a supersaturated solution in order to crystallize 2-O-α-D-glucopyranosyl-L-ascorbic acid.

7. The process of claim 6, wherein said 2-O-α-D-glucopyranosyl-L-ascorbic acid is crystallized at a temperature in the range of 20°–60° C.

* * * * *